United States Patent [19]

Kazan et al.

[11] 4,070,456

[45] Jan. 24, 1978

[54] COMPOSITIONS CONTAINING DIOCTYL CALCIUM SULFOSUCCINATE

[75] Inventors: John Kazan, Somerville, N.J.; Robert Arnold Nash, Spring Valley, N.Y.

[73] Assignee: American Cyanamid Company, Stamford, Conn.

[21] Appl. No.: 673,838

[22] Filed: Apr. 5, 1976

[51] Int. Cl.² .................... A61K 47/00; A61K 31/225
[52] U.S. Cl. ..................................... 424/173; 424/313
[58] Field of Search .............................. 424/313, 173

[56] References Cited

U.S. PATENT DOCUMENTS

| | | | |
|---|---|---|---|
| 2,870,061 | 1/1959 | Huggins | 424/313 |
| 2,885,322 | 5/1959 | Klotz | 424/313 |
| 3,035,973 | 5/1962 | Klotz | 424/313 |

*Primary Examiner*—Sam Rosen
*Attorney, Agent, or Firm*—Edward A. Conroy, Jr.

[57] ABSTRACT

Compositions comprising dioctyl calcium sulfosuccinate in a mixture of non-aqueous, i.e. oil, solvents are disclosed as being resistant to crystallization at low temperatures. Dosage units comprising gelatin capsules containing said compositions are also disclosed. The compositions of this invention are useful as fecal softeners.

10 Claims, No Drawings

100# COMPOSITIONS CONTAINING DIOCTYL CALCIUM SULFOSUCCINATE

BACKGROUND OF THE INVENTION

The present invention pertains to compositions containing dioctyl calcium sulfosuccinate, also known as S-calcium bis(2-ethylhexyl) sulfosuccinate. More particularly, this invention pertains to compositions comprising a solution of dioctyl calcium sulfosuccinate in a mixture of non-aqueous solvents. The invention also pertains to an improved dosage unit comprising a gelatin capsule containing said compositions.

Compositions comprising dioctyl calcium sulfosuccinate dissolved in oils, such as corn oil, peanut oil, cotton seed oil, and the like, as well as equivalent non-aqueous solvents such as polyethylene glycols 200-400, containing up to 10% by volume of glyceryl monooleate in soft gelatin capsules are disclosed by Klotz in U.S. Pat. No. 3,035,973 as fecal softeners. However, the preferred compositions of Klotz, which utilize corn oil, cannot be stored at temperatures below 10° C. without crystallizing, or solidifying. Furthermore, allowing the solidified or crystallized compositions to warm to room temperature does not cause them to revert to free-flowing fluids. Often the compositions disclosed by Klotz gel or crystallize under ambient conditions (20°-25° C.).

There is a need, therefore, for a composition comprising dioctyl calcium sulfosuccinate in a non-aqueous solvent or mixture of solvents which will either resist solidification or crystallization at temperature below 10° C., or revert to clear free-flowing fluids on warming to ambient conditions. Preferably, the solution should neither solidify nor crystallize on prolonged storage below 10° C. and be a clear free-flowing fluid under ambient conditions. There is also a need for a dosage unit containing dioctylsulfosuccinate in a non-aqueous solvent or mixture of solvents in a gelatin capsule which will either resist solidification or crystallization at temperatures below 10° C. or revert to clear free-flowing fluids on warming to ambient conditions.

SUMMARY OF THE INVENTION

We have discovered compositions comprising solutions of from about 40% to about 60% by weight of dioctyl calcium sulfosuccinate, from about 10% to about 40% by weight of a polyol ester of mixed caprylic and capric acids and about 20% to about 30% by weight of glyceryl monooleate. The preferred compositions of this invention comprise solutions of from about 45% to about 55% by weight of dioctyl calcium sulfosuccinate, from about 20% to about 35% by weight of a propylene glycol dicaprylate/dicaprate, and from about 20% to about 25% by weight of glyceryl monooleate. A particularly preferred composition of this invention comprises a solution of about 50% by weight of dioctyl calcium sulfosuccinate, from about 25% to about 30% by weight of a propylene glycol dicaprylate/dicaprate, and from about 20% to about 25% by weight of glyceryl monooleate.

We have also discovered an improved dosage unit comprising a gelatin capsule containing one of the above-mentioned compositions. The preferred dosage unit comprises a soft gelatin capsule containing one of the above-mentioned preferred compositions. The compositions and dosage units of the present invention are superior to those of the prior art in that they resist solidification and crystallization on prolonged storage at 5° to 7° C. The compositions and dosage units of the present invention are also superior to those of the prior art in that if crystallization is induced by storage at low temperatures the compositions revert to clear free-flowing fluids on warming to ambient conditions.

DESCRIPTION OF THE PREFERRED EMBODIMENTS

Dioctyl calcium sulfosuccinate can be prepared by the procedure of Example 1 of U.S. Pat. No. 3,035,973, which is incorporated herein by this reference thereto. The term "polyol" as used herein is defined as propylene glycol and glycerol. The expression "propylene glycol dicaprylate/dicaprate" as used herein is defined as a diester of a mixture of naturally derived caprylic and capric acids which is known commercially as Neobee ® M-20 (PVO International Inc., Boonton, New Jersey). The expression "caprylic/capric triglyceride" as used herein is defined as a low molecular weight fraction of palm oil consisting generally of mixed esters of caprylic and capric acids which is known commercially as Neobee ® M-5.

As used herein "soft gelatin capsule" is defined as a gelatin capsule containing a plasticizing agent such as glycerine, sorbitol, 1,2,6-hexanetriol, or equivalent polyhydroxy compounds, or mixtures thereof, in the capsule wall. The concentration of dioctyl calcium sulfosuccinate employed in the capsule ranges from about 40 to about 240 mgs. While the dosage unit of the present invention is in the form of a gelatin capsule, it is obvious the compositions of this invention may also be packaged in suitable containers such as glass bottles, polyethylene bottles, polyethylene bags, and the like, for administration by means of a spoon.

We have found that the compositions of this invention become more susceptible to crystallization in the presence of water. Thus, the compositions of this invention are preferably stored in water-impermeable capped glass containers. We have also found that the preferred compositions of this invention can be stored for long periods of time at −5° to −7° C. in water-impermeable glass bottles, without solidification, and become clear free-flowing liquids on warming to room temperature.

In preparing the compositions of this invention a solution containing dioctyl calcium sulfosuccinate in isopropanol is added to an appropriate mixture of either propylene glycol dicaprylate/dicaprate, or caprylic/capric triglyceride, and glyceryl monooleate in sufficient quantity to obtain the desired final composition on subsequent removal of the isopropanol by heating under vacuum.

The following examples are illustrative of this invention but they are not intended to be limitative thereof. All samples mentioned in the examples which follow were stored in capped bottles. All parts and percentages mentioned therein are by weight.

Example 1

| | | |
|---|---|---|
| A. | Dioctyl calcium sulfosuccinate in isopropanol (50% real) | 500 grams |
| | Propylene glycol dicaprylate/dicaprate | 150 grams |
| | Glyceryl monooleate | 100 grams |
| B. | Dioctyl calcium sulfosuccinate in isopropanol (50% real) | 500 grams |
| | Propylene glycol dicaprylate/dicaprate | 125 grams |
| | Glyceryl monooleate | 125 grams |

The solution of dioctyl calcium sulfosuccinate in isopropanol was dissolved in the mixtures of propylene glycol dicaprylate/dicaprate and glyceryl monooleate in the amounts specified in A and B, above, and the resulting solutions were heated at 125°–130° C. under vacuum to remove the volatiles. After removal of the volatiles, compositions A and B contained 50% dioctyl calcium sulfosuccinate, 30% propylene glycol dicaprylate/dicaprate, and 20% glyceryl monooleate; and 50% dioctyl calcium sulfosuccinate, 25% propylene glycol dicaprylate/dicaprate, and 25% glyceryl monooleate, respectively.

After storing for one month at 5° C. and at −5° C. no solidification or gelling was observed with either composition A or B. All samples were clear free-flowing liquids on warming to room temperature (22° C.). Composition A was also stored for 8 months at −5° C. All samples remained fluid but developed a slight haze over this period. All samples became clear free-flowing liquids on allowing them to warm to room temperature.

EXAMPLE 2

The composition of Example 1-A after removal of the volatiles was stored in soft gelatin capsules at 5°–7° C. for 2 weeks. After this period microscopic examination of the solution within the capsules showed no evidence of crystallization.

Example 3

| | |
|---|---|
| Dioctyl calcium sulfosuccinate in isopropanol (50% real) | 500 grams |
| Caprylic/capric triglyceride | 150 grams |
| Glyceryl monooleate | 100 grams |

The procedure of Example 1 was used to prepare a solution which contained 50% dioctyl calcium sulfosuccinate, 30% caprylic/capric triglyceride, and 20% glyceryl monooleate after removal of the volatiles.

Samples of this composition were stored at 5° C. and −7° C. for a period of 3 months. The samples stored at 5° C. remained clear. All samples became free-flowing fluids on warming to ambient conditions. The samples stored at −7° C. solidified. Upon warming to room temperature all samples became clear free-flowing liquids.

EXAMPLE 4

The composition of Example 3 was stored in gelatin capsules at 5°–7° C. for 2 weeks in a refrigerator. After this period microscopic examination of the solution within the capsule showed that it was free from crystals.

Example 5

| | |
|---|---|
| Dioctyl calcium sulfosuccinate in isopropanol (50% real) | 500 grams |
| Propylene glycol dicaprylate/dicaprate | 100 grams |
| Glyceryl monooleate | 150 grams |

The procedure of Example 1 was used to prepare a solution containing 50% dioctyl calcium sulfosuccinate, 20% propylene glycol dicaprylate/dicaprate, and 30% glyceryl monooleate. When samples of this composition were stored at 5° C. no solidification or gelling was observed. All samples became free-flowing liquids on warming to room temperature.

Example 6

| | |
|---|---|
| Dioctyl calcium sulfosuccinate in isopropanol (50% real) | 500 grams |
| Corn oil | 250 grams |

The procedure of Example 1 was used to prepare a solution containing 50% dioctyl calcium sulfosuccinate and 50% corn oil. Samples of this composition gelled after storing at −7° to 30° C. in from 1 to 30 days. Allowing the gelled samples to warm to room temperature did not revert them to a free-flowing fluid.

This example illustrates an inoperative composition of the prior art.

Example 7

| | |
|---|---|
| Dioctyl calcium sulfosuccinate in isopropanol (50% real) | 500 grams |
| Propylene glycol dicaprylate/dicaprate | 250 grams |

The procedure of Example 1 was used to prepare a solution containing 50% dioctyl calcium sulfosuccinate and 50% propylene glycol dicaprylate/dicaprate. Samples of this composition gelled after storing at room temperature. Refrigeration of samples of this composition resulted in complete solidification of the samples within two days. Allowing the refrigerated samples to stand at room temperature for 24 hours did not revert them to free-flowing fluids.

This composition is outside of the scope of this invention and inoperative.

Example 8

| | |
|---|---|
| Dioctyl calcium sulfosuccinate in isopropanol (50% real) | 500 grams |
| Corn oil | 225 grams |
| Glyceryl monooleate | 25 grams |

The procedure of Example 1 was used to prepare a solution containing 50% dioctyl calcium sulfosuccinate, 45% corn oil, and 5% glyceryl monooleate. Samples of this composition gelled after storage at −7° to 30° C. in from 1 to 30 days. The gelled samples did not revert to free-flowing fluids on warming to room temperature.

This example also illustrates an inoperative composition of the prior art.

Example 9

| | |
|---|---|
| Dioctyl calcium sulfosuccinate in isopropanol (50% real) | 500 grams |
| Corn oil | 150 grams |
| Propylene glycol dicaprylate/dicaprate | 100 grams |

The procedure of Example 1 was used to prepare a solution containing 50% dioctyl calcium sulfosuccinate, 30% corn oil, and 20% propylene glycol dicaprylate/dicaprate. Samples of the composition of this example solidified after storage at 7° C. for 2 days. Allowing the solidified samples to stand at room temperature for 24 hours did not revert them to free-flowing fluids.

A sample of the unreverted composition was warmed to 50° C. to clarify it and cooled to room temperature. After 5 days at room temperature the sample was about 10–20% gelled.

This composition is outside of the scope of this invention and inoperative.

Example 10

| | |
|---|---|
| Dioctyl calcium sulfosuccinate in isopropanol (50% real) | 500 grams |
| Glyceryl monooleate | 250 grams |

The procedure of Example 1 was used to prepare a solution containing 50% dioctyl calcium sulfosuccinate and 50% glyceryl monooleate. Samples of this composition remained fluid when stored at 5° C. but solidified at −5° C. Allowing the stored samples to warm to room temperature reverted them to free-flowing fluids. However, this composition has a viscosity which is too high for practical use.

This composition is outside of the scope of this invention and inoperative for practical purposes because of the high viscosity.

We claim:

1. A composition comprising from about 40% to about 60% of dioctyl calcium sulfosuccinate, from about 10% to about 40% of a solvent consisting essentially of a polyol ester of mixed caprylic and capric acids, and from about 20% to about 30% of glyceryl monooleate.

2. A composition in accordance with claim 1 wherein said ester is a propylene glycol dicaprylate/dicaprate.

3. A composition in accordance with claim 1 wherein said ester is a caprylic/capric triglyceride.

4. A composition in accordance with claim 2 comprising from about 45% to about 55% of dioctyl calcium sulfosuccinate, from about 20% to about 35% of said propylene glycol dicaprylate/dicaprate, and from about 20% to about 25% of glyceryl monooleate.

5. A composition in accordance with claim 4 comprising about 50% of dioctyl calcium sulfosuccinate, from about 25% to about 30% of said propylene glycol dicaprylate/dicaprate, and from about 20% to about 25% of glyceryl monooleate.

6. A composition in accordance with claim 3 comprising about 50% of dioctyl calcium sulfosuccinate, from about 25% to about 30% of said caprylic/capric triglyceride, and from about 20% to about 25% of glyceryl monooleate.

7. A dosage unit consisting of a soft gelatin capsule containing 40–240 mgs. of dioctyl calcium sulfosuccinate in a composition in accordance with claim 1.

8. A dosage unit consisting of a soft gelatin capsule containing 40–240 mgs. of dioctyl calcium sulfosuccinate in a composition in accordance with claim 4.

9. A dosage unit consisting of a soft gelatin capsule containing 40–240 mgs. of dioctyl calcium sulfosuccinate in a composition in accordance with claim 5.

10. A dosage unit consisting of a soft gelatin capsule containing 40–240 mgs. of dioctyl calcium sulfosuccinate in a composition in accordance with claim 6.

* * * * *